(12) United States Patent
Antheunisse et al.

(10) Patent No.: US 7,052,729 B2
(45) Date of Patent: May 30, 2006

(54) STABLE OIL IN WATER EMULSION

(75) Inventors: Willem Antheunisse, Vlaardingen (NL); Elisabeth Cornelia Bouwens, Vlaardingen (NL); Yvonne Evelien Bruggeman, Vlaardingen (NL)

(73) Assignee: Conopco, Inc., Edgewater, NJ (US)

( * ) Notice: Subject to any disclaimer, the term of this patent is extended or adjusted under 35 U.S.C. 154(b) by 245 days.

(21) Appl. No.: 10/457,789

(22) Filed: Jun. 10, 2003

(65) Prior Publication Data

US 2004/0009285 A1  Jan. 15, 2004

(30) Foreign Application Priority Data

Jun. 24, 2002 (EP) ................... 02077482

(51) Int. Cl.
*A23D 7/00* (2006.01)

(52) U.S. Cl. ...................... 426/602; 426/604

(58) Field of Classification Search ........ 426/602–604, 426/577

See application file for complete search history.

(56) References Cited

U.S. PATENT DOCUMENTS 5,928,706 A * 7/1999 Gibson et al. ............. 426/656

2002/0028197 A1 * 3/2002 Fitchett .................... 424/94.4

FOREIGN PATENT DOCUMENTS

| EP | 0426434 | * | 10/1990 |
| EP | 0 426 434 A1 | | 5/1991 |
| FR | 2811911 | * | 7/2000 |
| FR | 2 811 911 | | 1/2002 |
| WO | WO 96/03440 | | 2/1996 |
| WO | WO 00/40098 | * | 7/2000 |

OTHER PUBLICATIONS

Adsorbent antioxidant provides optimum frying in restaurant and fast food fryers, Eur. J. Lipid Sci. Technol. 102 (2000) 560-565.

B. Friedman, Fat and Cholesterol Reduced Foods Technologies and Strategies, New Control of Frying Process Provides Major Reduction of Oil in Food, Advances in Applied Biotechnology Series, vol. 12, pp. 141-152.

The Merck Index, An Encyclopedia of Chemicals and Drugs, Ninth Edition (1976), Entry 1531 and 1532, pp. 197-198.

* cited by examiner

*Primary Examiner*—Carolyn Paden
(74) *Attorney, Agent, or Firm*—Michael P. Aronson

(57) ABSTRACT

The invention relates to a method of preparing stable oil in water emulsions wherein a ferulyolated compound is at least partly oxidized during or after formation of the oil in water emulsion.

9 Claims, No Drawings

STABLE OIL IN WATER EMULSION

FIELD OF THE INVENTION

The invention relates to an oil in water emulsion comprising a crosslinked composition, especially cross linked pectin.

BACKGROUND TO THE INVENTION

Certain polymers containing ferulic acid groups attached to their backbone are known to be gellable by oxidation. An example of these polymers is pectin. The gelling may be achieved by addition of an appropriate amount of an enzyme of the oxidase type e.g. laccase or peroxidase. The application of the resulting gels in food stuff is known.

WO-A-00/40098 discloses a fat replacer comprising a pectin composition wherein the pectin composition comprises at least a population of pectin which is covalently crosslinked. A process is disclosed wherein this crosslinked pectin is incorporated in the food stuff such as yoghurt, mayonnaise, ice cream. Such products are emulsions of oil in water. The resulting products, though more viscous or partly gelled, were found to be unstable upon storage at 4 to 20° C. for about 4 days. This was evidenced by water separation (syneresis) and phase separation of the emulsion after prolonged storage.

It is an object of the invention to provide products that show improved stability compared to the products of the art. Preferably the products are stable against syneresis for at least 40 days at from 4 to 30° C., preferably from 4 to 20° C.

SUMMARY OF THE INVENTION

It has surprisingly been found that the moment at which the crosslinking by oxidation takes place, determines the stability of the final oil in water emulsion.

Therefore the invention relates to a process for the preparation of an oil in water emulsion comprising a covalently crosslinked ferulyolated compound wherein a ferulyolated compound is at least partly oxidized during or after formation of the oil in water emulsion.

In a further aspect the invention relates to a product obtainable by this process.

In another aspect the invention relates to a food product comprising the emulsion.

DETAILED DESCRIPTION OF THE INVENTION

In the context of the invention, the terms "fat" and "oil" are used interchangeably. The term oil encompasses both triglyceride oils and diglyceride oils.

For the purpose of the current invention, wt % is defined as weight percent on total product weight unless otherwise is indicated.

Stable emulsions are defined as less than 3 wt %, preferably less than 2 wt %, more preferably no release of water or oil coming out of the product so that no phase separation was observed. A small amount of phase separation can be tolerated up to about 3 wt %.

The term oxidant is used to indicate an oxidising agent, which can be either a chemical oxidising agent or an enzyme. An enzyme can be used alone or in combination with a co-oxidant such as hydrogen peroxide.

The invention concerns the preparation of an oil in water emulsion. Such emulsions comprise an aqueous phase and a fat phase. The aqueous phase is the continuous phase. The oil phase is the dispersed phase. Also covered are products comprising more than one dispersed (oil) phase and products wherein the dispersed oil phase comprises a dispersed phase itself.

The process according to the invention is based on the at least partial oxidation of ferulic acid groups of a ferulyolated compound. This oxidation leads to gel formation or at least increased viscosity of the aqueous phase. The gel forming capacity of e.g. pectins is for examples described in WO-A-98/22513 and WO-A-00/40098 and WO-A-96/03440.

Ferulic acid groups (4-hydroxy-3-methoxy-cinnamyl-groups) are known to be capable of crosslinking in the presence of certain oxidants (e.g. Oosterveld et al; oxidative crosslinking of pectic polysaccharides from sugar beet pulp, Carbohydrate research 328; 199–207, 2000). In the oxidation process a new covalent bond is formed between two individual ferulic acid groups.

The compound comprising ferulyolated groups is preferably a polymer, more preferably a polysaccharide. Examples of suitable polymers include pectin, arabinan, galactan, cellulose derivatives, galactomannans such as guar gum, locust bean gum, starches or other polymers comprising hydroxyl groups which can be esterified to a ferulic acid group.

The polymers comprising ferulic acid groups can be naturally boccurring or synthesised polymers. Examples of naturally occurring polymers with ferulic acid groups are sugar beet pectin and arabinoxylanes isolated from cereals.

Synthetic processes to prepare polymers with ferulic acid groups generally include esterification of ferulic acid to a free hydroxyl group situated on the polymer backbone or on a sugar substituent.

In a highly preferred embodiment, the ferulyolated compound is a pectin, even more preferably sugar beet pectin. The principal building units of pectin are smooth homogalacturonic regions and rhamnified hairy regions in which most neutral sugars are located. Arabinose is the predominant neutral sugar. Galactose is present in rhamnogalacturonan. 50–55% of the ferulic acid groups are linked to arabinose units and about 45–50% of the ferulic acid groups are linked to galactose residues.

Preferably 15 to 80% of all ferulic acid groups are oxidised in the final emulsion, after oxidation.

It is preferred that the majority of ferulic acid groups is not oxidised before the oxidation. Even more preferred before oxidation at most 10% of all ferulic acid groups are oxidised.

In the process of the invention it is essential that the oxidation of the ferulic acid groups takes place during or after formation of the oil in water emulsion. It was found that addition of pectin oxidised before emulsion formation, did not lead to products with increased stability.

The oxidation takes place during or after the formation of the oil in water emulsion. Preferably the oxidation takes place during or shortly after the formation of the oil in water emulsion, thus stabilising the emulsion. Shortly after means before the emulsion shows any signs of destabilisation such as phase separation. Generally this is within several minutes after the emulsion has formed but larger time periods can be used, depending on the specific circumstances.

Without wishing to be bound by any theory it is believed that the oxidation leads to network formation whereby the dispersed oil phase is trapped in this network which at least viscosities the aqueous phase. Addition of oxidized compound as is known from the prior art, does not lead to entrapment of oil droplets in the network and hence does not impart the desired stability.

The oxidation may be accomplished by the action of a powerful chemical oxidant such as potassium periodate, potassium permanganate, or potassium ferricyanide.

Alternatively the oxidation can be accomplished by use of an oxidising enzyme such as a peroxidase, a polyphenol oxidase e.g. catechol oxidase, tyrosinase, or a laccase.

Peroxidases can be divided into those originating from plants, fungi or bacteria and those originating from a mammalian source such as myeloperoxidase and lactoperoxidase (LPO).

Laccases are obtainable from a variety of microbial sources notably bacteria and fungi (including filamentous fungi and yeasts), and suitable examples of laccases include those obtainable from strains of *Aspergillus, Neurospora* (e.g. *N. crassa*), *Prodospora, Botrytis, Collybia, Fomes, Lentinus, Pleurotus, Trametes*[some species/strains of which are known by various names and/or have previously been classified within other genera], *Polyporus, Rhizoctonia, Coprinus, Psatyrella, Myceliophtora, Schytalidium, Phlebia* or *Coriolus*.

Preferred enzymes are selected from the group comprising horseradish peroxidase, soy bean peroxidase, *Arthromyces ramosus* peroxidase and laccases that show a redox potential of more than 400 mV, preferably more than 550 mV as described in E. Solomon et al, Chem Rev, 1996, p 2563–2605.

The extent of oxidation of the ferulyolated compound can be measured by spectrophotometric determination of the absorbance at 375 nm. Absorption at this wavelength is characteristic for an oxidised ferulic acid group.

In case a chemical oxidant is applied, the oxidant is preferably added in the form of a diluted aqueous solution.

In case an enzymatic oxidising system is applied, the enzyme is preferably added in the form of a solution or a dispersion in an aqueous buffer system. The enzymes cited above are suitable enzymes. Some enzymes, such as peroxidases require the presence of a co-oxidant such as hydrogen peroxide for their activity. The co-oxidant is preferably added separately from the enzyme that requires its presence.

The amount of enzyme added is expressed in terms of activity units. Preferably enzyme is present in excess. The amount of enzyme added is preferably such that fast crosslinking occurs. For a peroxidase the amount of enzyme added is preferably from 10 to 100.000 units ABTS activity per ml of liquid.

The oxidation is preferably carried out at a temperature of from −20° C. to 80° C., preferably 4 to 70° C. It will be appreciated that the best temperature depends on the oxidation system that has been chosen.

The simultaneous emulsification and oxidation can be obtained in several ways. According to one embodiment, an oxidising agent is added to the aqueous phase immediately whereafter the oil phase is included in the process. Emulsification then takes place while the ferulyolated compound in the aqueous phase is oxidised.

According to another embodiment the oxidising agent is added to the aqueous phase which already comprises ferulyolated compound, while at the same time the oil phase is added under stirring.

An emulsion may also be mixed with the oxidising agent and the oxidation would take place after the emulsion was prepared as for example in pre-emulsions. Oxidation then takes place to form stable end products.

Preferably the emulsion has not fully formed before oxidation. However, the ingredients may have been mixed to form a pre-emulsion.

The amount of ferulyolated compound is preferably from 0.5 to 20 wt %. Lower amounts were found not to provide sufficient firmness and storage stability was unsatisfactory. Higher amounts often do not dissolve at a satisfactory level and may lead to inclusion of the oxidant by oxidised polymers. This may inactivate the oxidant and may lead to phase separation. More preferably the amount of ferulyolated compound is from 0.5 to 10 wt %, more preferred 0.5 to 4 wt %, even more preferred from 0.5 to 2 wt % on total emulsion weight.

The emulsion preferably comprises from 1 to 90 wt % fat, more preferred from 1 to 70 wt % fat, even more preferred from 5 to 60 wt % fat.

In a further aspect the invention relates to an emulsion obtainable by the process according to the invention. Such emulsions were found to show advantageous stability against syneresis or phase separation.

Another advantage of the products obtained by the claimed process is that they show a homogeneous distribution of dispersed phase in aqueous phase and a homogeneous water/gel structure.

The emulsion can be used as a final product and may be sold as such. Alternatively the emulsion is included in a food product. Therefore in a further aspect the invention relates to a food product comprising the emulsion prepared according to the process of the invention.

The emulsion may be prepared separately and then included in the food product, but alternatively the emulsion is prepared in situ during the preparation of the food product.

Food products wherein the emulsion may suitably be incorporated are preferably selected from the group comprising dairy products, such as milk, ice cream, spreadable products such as margarine, butter, low fat spreads, sauces, dressings, and mayonnaise; acidified dairy products, such as dressings containing casein; and non dairy food products, such as salad dressing (vinaigrette), other dressings, sauces such as white, brown and hollandaise sauce, and soup.

The oil or fat used may be dependent on the type of product. The fat is preferably selected from the group comprising sunflower oil, coconut oil, butter fat, rapeseed oil, olive oil, peanut oil or oils extracted from plant or flower material such as rose oil, and combinations thereof. Also fractionated oils are encompassed in the invention.

The emulsion further comprises optional ingredients such as protein, salt, flavour components, colourants, emulsifiers, acidifying agents, (co)-oxidants such as hydrogen peroxide, and the like.

The invention is illustrated in the following non-limiting examples.

EXAMPLES

General

Sources of Ingredients

1. Sugar Beet Pectin

Extracted from sugar beet.

Commercially available from CP Kelco (Denmark) (GENU beta pectin type BETA)

2. Enzyme/Hydrogen Peroxide:

Peroxidase non-GM, food grade Biobake Wheat from Quest, the Netherlands.(Specific activity 566 units per mg at pH 5).

Peroxidases need hydrogen peroxide as cofactor (0.0035%=1 mM). Hydrogen peroxide used is 30% solution of Merck, Germany. Glucose oxidase, non-GM, food grade from Amano in combination with glucose and Biobake wheat were used for some examples.

3. Determination of Water Release and Oil Release

Calibrated 50 ml tubes were completely filled with product. Water release (water layer on bottom of tube) was determined. The weight of the product was determined by weighing the empty and the filled tube. Water release is expressed as ml water released per gram of product. Oil release (oil layer on top of product) was determined. Oil release is expressed as g oil released per gram of product.

Alternatively, oil and water release can be determined by visible inspection.

4. Activity Assay (ABTS Assay)

Add 100 µl 20 mM ABTS (2,2'-azino-bis(3-ethylbenzothiazoline-6-sulfonic acid (ABTS) stock solution made in indicated buffer) to 880 µl 25 mM phosphate buffer, pH 6.0. Incubate for 5' at 30° C. Add 10 µl 100 mM hydrogen peroxide. Start the reaction by addition of 10 µl enzyme (diluted in such a way that a linear curve could be measured). Measure the formation of ABTS radical at 414 nm using a spectrophotometer.

Specific activity is defined as: pmol ABTS oxidised per minute per mg protein at pH 6.0.

The activity can also be measured at pH 5.0

Example 1

Mayonnaise based dressings with different amounts of oil.

Dressings were made with 4 different oil content from 0 to 70%.

By varying water and increasing oil dressings were made and contain the following ingredients:

| Dressings with sugar beet-pectin | 1 | 2 | 3 | 4 | 5 | 6 |
|---|---|---|---|---|---|---|
| | | | | % | | |
| B-carotene, 0.2% sol. | | | All: 0.2 | | Both: 0 | |
| Water | 81 | 46 | 31 | 11 | 55.8 | 53.8 |
| Oil, sun flower | 0 | 35 | 50 | 70 | 35.0 | 35.0 |
| Mustard | | | All: 2 | | Both: 0 | |
| Egg-yolk, 89/11 | | | All: 3.60 | | Both: 0 | |
| Vinegar sprit, 12% | | | All: 3.5 | | Both: 3.0 | |
| Sugar | | | All: 5.5 | | Both: 1.96 | |
| Salt | | | All: 1.25 | | Both: 2.06 | |
| peroxide | | | All: 2.00 | | Both: 0.006 | |
| Soy bean peroxidase (Biobake) | | | | | All: 0.3 | |
| Pectin # | 2 | 1.7 | 1 | 1 | Both: 1.8 | |
| Eggs (whole eggs) | | | All: 0 | | 1 | 3 |
| K-sorbate | | | All: 0 | | Both: 0.09 | |
| EDTA | | | All: 0 | | Both: 0.012 | |
| Na-caseinate | | | All: 0 | | Both: 1.00 | |
| Xanthan gum | | | All: 0 | | Both: 0.09 | | stock solution of sugar beet pectin 6% can be used which is formed as follows:
Add 60 g sugar beet pectin in 1 L water, stir intensively while adding about 50 ml 1 M NaOH dropwise until pH 5 is reached. The concentrations of pectin set out in the ingredient list above are the % wt pectin/wt product.

Process:

The ingredients were mixed for a few minutes in a Hobart mixer, turrax mixer or colloid mill (Frima). We used a turrax mixer for samples 1–4 and a colloid mill for samples 5–6.

For samples 1–4, the enzyme (biobake) and peroxide were added as the last ingredients while all others were being mixed. To prepare samples 5–6, eggs, casein, NaCl, sugar, xanthan gum, water, pectin and oil were mixed (step 1), then biobake and peroxide were added and mixed (step 2) and then, as a last step (step 3), vinegar, K-sorbate and EDTA were mixed which caused a pH decrease. This pH drop has to occur after the emulsion is formed and after pectin cross-linking, to prevent syneresis.

Reference samples without pectin cross-linking showed syneresis (water on top or at the bottom) and in some cases, especially at low amounts of oil, oil-water phase separation (oil on top). The samples made with cross-linked pectin were very stable and homogeneous (no water or oil on top or bottom).

Rheological data for the product of sample 5 made with cross linked pectin were compared with those for a sample with similar ingredients, only with starch instead of pectin. The results are shown in the following table:

| | G' | G'' | critical strain |
|---|---|---|---|
| Sample 5 with cross-linked pectin | 1250 | 270 | 0.7 |
| Sample with starch (no pectin) | 770 | 105 | 1.27 |

The difference in critical strain is an especially important parameter in relation to mouth-feel. The critical strain of the product with cross-linked pectin is 0.7, which is very good, while the product with starch showed a critical strain of 1.27, which is very high.

Example 2

Hollandaise Sauce.

The final composition of the Hollandaise sauce contains 0.9% w/w sugar beet pectin. This can be varied as desired to make a sauce with the optimal thickness.

The product was prepared by mixing three stock solutions A, B and C using a small scale rotor stator unit of about 10 ml volume, a mixer with four small pins and a smooth end. The solutions are: A) oil phase, B) enzyme phase and C) peroxide phase, prepared with the ingredients as given in the last three columns of the table. The three solutions were separately pumped and were mixed in the rotor stator unit. The oil phase, solution A was pumped with 1.65 l/hr while solutions B was pumped with 0.73 l/hr and C with 0.6 l/hr The shear applied was 3000 rpm ($\cong$shear 9000 sec$^{-1}$), the residence time of the product 12 seconds. Products were made at ambient temperature.

All ingredients are listed below:

| Hollandaise sauce structured with sugar beet-pectin | % | Stock solutions | | |
|---|---|---|---|---|
| | | A | B | C |
| Hardened vegetable oil (RP oil) | 55 | 55 | | |
| water | 15 | | 5 | 9.68 |
| egg yolk, 89/11 SEY (partly fermented) | 6.06 | | 6.06 | |
| sugar | 0.50 | | 0.50 | |
| Onion powder | 0.33 | | 0.33 | |
| lactic acid (88%) | 0.21 | | | 0.21 |
| Flavours, (a.o. hollandaise flav. pepper) | 0.39 | 0.03 | 0.36 | |
| peroxide (30%) | 0.02 | | | 0.02 |
| Soy bean peroxidase (Biobake). | 0.40 | | 0.40 | |

-continued

| Hollandaise sauce structured with sugar beet-pectin | % | Stock solutions | | |
|---|---|---|---|---|
| | | A | B | C |
| 4% sugar beet pectin in 0.2M Na-acetate pH5 | 22.0 | | 12.0 | 10.0 |
| beta carotene 0.2% | | 0.1 | 0.2 | |
| Total | 100.0 | 55 | 25 | 20 |

Example 3

Salad Dressings (1) Vinaigrette:

Vinaigrette was made from oil, spices, vinegar, pectin and enzyme, the spices can be varied as desired, the amount of vinegar and water was similar to commercial available product formulation (see below). Pectin concentration was varied in the final product from 0.5% to 2% w/v. Biobake was added (varying from 0.05 to 1% w/v) dependent on the preparation time and hydrogen peroxide was added generally between 0.1 mM (0.0003%) and 2 mM (0.006%).

A general commercial vinaigrette contains:

| Ingredients | wt % |
|---|---|
| B-carotene, 0.2% sol. | 0.08 |
| Water | 63 |
| Oil, rape seed | 15 |
| Seasoning flav. | 0.10 |
| Spice flavour | 0.03 |
| Onion pieces, dried | 0.60 |
| Paprika skin | 0.25 |
| Parsley, extra fine | 0.10 |
| Vinegar, 10% | 10.00 |
| Sodium citrate | 0.35 |
| Sugar | 5.50 |
| Salt | 2.00 |

The flavours used can be any desired flavour, or fresh flavours, to make your own vinaigrette. Examples of flavours are: balsamic, cheese, mustard, wine, parsley.

(2) Salad Dressing

| | % | weight (g) |
|---|---|---|
| Salt | 1.00 | 6.00 |
| Sugar | 4.00 | 24.00 |
| mustard (French) | 0.5 | 0.15 |
| Vinegar, 12% | 7.50 | 45.00 |
| Water | 17.325 | 107.00 |
| chicken broth (Knorr 17 g/L) | 20.00 | 120.00 |
| Olive oil (Bertolli gentile extra virgin) | 19.00 | 114.00 |
| Sugar beet pectin 6% pH 5.5 | 30.00 | 180.00 |
| Biobake | 0.08 | 0.5 |
| hydrogen peroxide (1M) | 0.075 | 0.45 |
| red pepper chopped | 0.33 | 2.00 |
| Parsley, extra fine | 0.17 | 1.00 |
| vitamin C* | 0.02 | 0.12 |
| total | 100.0 | 600.1 |

*Vitamin C addition after cross linking of pectin (at the end)

The salad dressing can be made in a Hobart mixer (stand 1, 5–10 minutes) or using an ultra-turrax (15000 rpm/5 minutes):

All the ingredients except the oil, hydrogen peroxide and vitamin C were mixed. The oil was added slowly while mixing, and hydrogen peroxide was then added and the mixture stirred (using a spoon or Hobart mixer) until the desired thickness was reached. Vitamin C was then added and the mixture briefly stirred. With this amount of pectin pH 5.5 and vinegar 12%, the pH of the salad dressing was 3.5.

The salad dressing with sugar beet pectin, made according to the invention was very stable (even after 2 months at 4° C.), while a reference salad dressing with similar ingredients without pectin, biobake and hydrogen peroxide was unstable (stored 24 hr at 4° C.).

Example 4

Product Formulation for white and brown sauce of wheat flour with sugar beet pectin.

White sauce, prepared by chefs is a time consuming process. Secondly, the regular sauces usually contain extra starch and or gelatin as thickening agent which are sometimes not preferred by the consumer. Therefore gelatin (and starch) can be replaced in the white sauce by the addition of sugar beet pectin, which can be crosslinked in situ by enzymes for an excellent heat and freeze stable thick sauce.

| Ingredients for sugar beet pectin based white and brown sauce | |
|---|---|
| Sugar beet pectin | 1–2% |
| Biobake Wheat | 0 to 0.5%, preferably 0.2–0.5% |
| Hydrogen peroxidase | 0.0035% |
| Wheat flour | 6.5% |
| Oil | 15% |
| Sodium chloride | 0.4% |
| Deionised water | 73% |
| Sodium acetate (0.1%–2%) | to pH 5 |

The amount of flour (from wheat, maize or other corns) can be varied, from 1% to 10% as desired. The amount of pectin can be varied from 1 for a thin sauce to 2.5% for a very thick sauce. The oil can be any vegetable oil (sun flower, rape seed) or instead of oil, fat as butter or margarine can be used. Sodium acetate (0.1% to max 2%) was added to adjust the pH to pH 5. Instead of sodium acetate addition, a pectin solution can be made which is adjusted to pH 5 using sodium hydroxide.

White sauce is made by gentle mixing of the flour with butter or oil, heating it (80–95° C.) and then mixing the water phase with pectin, sodium acetate, hydrogen peroxide and sodium chloride. Then, at temperature $\leq 80°$ C., enzyme is added. Alternatively, the hydrogen peroxide (and enzyme if needed) can be added at this stage (i.e. at temperature $\leq 80°$ C.). The mixture is then stirred until a thick sauce is formed. In the examples tested, the enzyme peroxidase was present in the flour and still very active after heating the flour and oil for ~5 minutes.

Alternatively, white sauce can be made by mixing the water phase of wheat flour pectin, enzyme, hydrogen peroxide, sodium acetate and sodium chloride with oil.

If intensive heat-treated flour is used, addition of Biobake Wheat was needed, for instance when brown sauce was made. Brown sauce is made by heating the flour and oil for 10–15 minutes and boiling until the colour of the flour is turned to brown. Then pectin and water were added. This decreases the temperature to ≦80° C. Then, addition of enzyme and hydrogen peroxide starts the gelation of the pectin to form a thick sauce. Without pectin cross-linking, the sauce stays very thin.

The White Sauce can be Mixed with:
milk and pectin to produce a béchamel sauce
milk and cheese, to produce a cheese sauce
mustard and wine to make a white wine sauce
(fresh) herbs to make a white herb sauce Alternatively, brown sauce can be made by heating the white sauce.

Example 5

Soup

Thick Soup was made by mixing soup ingredients with sugar beet pectin and enzyme and water.

As an example 10 g dried chicken soup ingredients (Cup a Soup, Unox) were mixed with 2.8 g sugar beet pectin and 0.3 g peroxidase (biobake). 140 ml hot water (70° C., the temperature at which general water is released from a soup machine) and 0.28 ml 1 M hydrogen peroxide were added and the soup was gently mixed with a spoon to homogeneously mix the powder. The soup thickened during stirring. It was clearly visible that the particles in the product with sugar beet pectin were homogeneously divided.

Reference samples were prepared (not according to the invention) wherein, in Example 5A, pectin was omitted and, in Example 5B, peroxidase was omitted while pectin was present. In both comparative examples, the particles precipitated.

Examples of soups are: chicken soup, vegetable soup, pea soup, asparagus soup, mushroom soup.

Example 6

Spreads

In experiments with sugar beet pectin, enzyme, hydrogen peroxidase and acidified milk protein, we found prevention of syneresis in samples where sugar beet pectin crosslinking was used according to the process of the invention. Sugar beet pectin crosslinking could be used in combination with addition of LBG or other thickening agents or used as the only thickening agent.

Sugar beet pectin crosslinking could be used for a variety of spreads:
normal margarine
low fat margarine
spreads with cheese
spreads with air Example 7

Avocado Dressing:

Process: All ingredients from the ingredient list were added except oil, vitamin C and hydrogen peroxide; peroxidase comes from fresh avocado. The ingredients were then mixed using an ultra-turrax (13500 rpm) while adding oil slowly and the product was cooled. Hydrogen peroxide was added in portions, while stirring gently, using a spoon or hobart mixer. Stirring continued until the desired thickness had been reached. Vitamin C was then added and gently mixed through the dressing with a spoon. The products were then pasteurised (10 min 70° C.) before storage.

If avocado puree is used and if the avocado puree does not contain enzyme activity, due to pasteurisation, partly fresh avocado can be added or soy bean peroxidase (=biobake wheat) at a dosage of 0.2% w/v.

Avocado dressing can be made with various amounts of oil and avocado. The recipe for a avocado dressing with 18% oil is as follows:

| thick sauce 18% fat | | |
|---|---|---|
| | (%) | (g) |
| water | 15 | 75 |
| flavours | 1.2 | 6 |
| salt | 1.5 | 7.5 |
| dextrose | 4 | 20 |
| K sorbate | 0.2 | 1 |
| EDTA | 0.0075 | 0.0375 |
| sugar beet pectin* (4% stock)) | 41 | 205 |
| enzyme (10% Biobake) | 0 | 0 |
| hydrogen peroxide (0.1M) | 0.8 | 4 |
| vitamin C | 0.2 | 1 |
| Sunflower oil | 18 | 90 |
| **Avocado puree (fresh mashed avocado) | 18 | 90 |
| spirit vinegar (12%) | 0.8 | 4 |
| lactic acid (80% solution) | 0 | 0 |
| citric acid (50% solution) | 0.16 | 0.8 |
| | 100.9 | 500 |

*stock solution 4% sugar beet pectin formed as follows: Add 40 g sugar beet pectin in 1 L water, stir intensively while adding about 50 ml 1M NaOH dropwise until pH 3.8 is reached Example 8

Cooking cream with pectin.

Mix one part of 2 wt % pectin with one part of commercially available cooking cream ('koksroom'), then crosslink the cream by adding 0.04% enzyme (biobake) and 1 mM hydrogen peroxide. The cream is stable against heating (100° C.) and acid.

Example 9

To find out the differences between dressings obtained according to the process disclosed in WO-A-00/40098, wherein pectin is crosslinked before the emulsion is formed or has formed, and the method according to the invention (in situ crosslinking) products were prepared according to both processes.

Dressings were made using the ultra turrax. All samples were mixed for 5 min (3 min slow speed, 2 min max speed). Samples were made of 100 ml. A stock solution of crosslinked sugar beet pectin was prepared by mixing pectin in hot water (using microwave) and stirred for 4 hr; then let it stand until it reached room temperature.

The final concentrations of the samples are:
35% w/w oil
3.6% w/w egg yolk
5.5% w/w sugar
1.255% w/w NaCl
3.55% w/w vinegar
2% w/w mustard and different amounts of pectin as mentioned below:

Addition to samples:
1a) 1% w/w Crosslinked sugar beet pectin (crosslinked in advance, as described in WO-A-00/40098; comparison example)

1b) 1% w/w sugar beet pectin, 0.05% w/w soy bean peroxidase (biobake) and 1 mM $H_2O_2$ (according to the invention)

1c) 1% sugar beet pectin (comparison example)

Results of Stability:

Sample 1b was stable after 7 days 4° C. or room temperature (nice homogeneous samples) while samples 1a, 1c were unstable, shown as phase separation: water at the bottom of the sample.

CSLM images were taken of the samples:

1a) Sample with pre-crosslinked pectin (comparison example) showed:
  inhomogeneous fluorescence indicating inhomogeneous water/gel structure
  inhomogeneous distribution of oil droplets (not random)

1b) in situ crosslinking according to the invention showed:
  homogeneous fluorescence indicating homogeneous water/gel structure
  homogeneous distribution of oil droplets (random)
  small air bubbles present in the sample 1c) Only pectin (comparison example):
  very inhomogeneous fluorescence indicating inhomogeneous water/gel structure
  very inhomogeneous distribution of oil droplets (not random)

CONCLUSION

Thus addition of pectin alone (sample c) or addition of pectin which is oxidised by enzymes in advance of formation of the oil in water emulsion (sample a) was not able to stabilize the oil in water emulsion and resulted in unstable products. Whereas addition of sugar beet pectin and enzyme (sample b) in the process according to the invention, which is making crosslinks in situ, resulted in stable emulsions.

The invention claimed is:

1. Process for the preparation of an oil in water emulsion comprising the steps of:
  i) forming an oil in water emulsion by adding an oil or oils to an aqueous phase under shear;
  ii) incorporating a ferulyolated polysaccharide in the oil in water emulsion at a level between about 0.5% to about 20% based on the total weight of the emulsion;
  iii) at least partially oxidizing the ferulyolated polymer to form covalent crosslinks by utilizing a chemical or enzymzatic oxidizing agent or agents during or after forming the oil in water emulsion.

2. Process according to claim 1 wherein the ferulyolated polysaccharide is a pectin.

3. Process according to claim 1 wherein the oxidizing step iii) is carried out at a temperature of from −20° C. to 40° C.

4. Emulsion obtainable by the process according to claim 1.

5. Food product comprising an emulsion according to claim 4.

6. Food product according to claim 5 wherein the food product is selected from the group consisting of dairy products such as milk and ice cream; spreadable products such as margarine, butter and low fat spreads; sauces; dressings; and mayonnaise.

7. Food products according to claim 5 wherein the food product is selected from the group consisting of acidified dairy products such as dressings containing casein.

8. Food products according to claim 5 wherein the food product is selected from the group consisting of non-dairy products such as salad dressings, other dressings, sauces and soup.

9. Process according to claim 1 wherein the oxidizing step iii) is carried out at a temperature of from 4° C. to 20° C.

* * * * *